(12) United States Patent
Soliman

(10) Patent No.: US 10,596,065 B2
(45) Date of Patent: Mar. 24, 2020

(54) TREATMENT OF ALLERGIES AND AUTOIMMUNE DISEASES

(71) Applicant: Nader Soliman, Rockville, MD (US)

(72) Inventor: Nader Soliman, Rockville, MD (US)

( * ) Notice: Subject to any disclaimer, the term of this patent is extended or adjusted under 35 U.S.C. 154(b) by 0 days.

(21) Appl. No.: 15/531,969

(22) PCT Filed: Dec. 9, 2015

(86) PCT No.: PCT/US2015/064685
§ 371 (c)(1),
(2) Date: May 31, 2017

(87) PCT Pub. No.: WO2016/094504
PCT Pub. Date: Jun. 16, 2016

(65) Prior Publication Data
US 2017/0326029 A1    Nov. 16, 2017

Related U.S. Application Data

(60) Provisional application No. 62/089,303, filed on Dec. 9, 2014.

(51) Int. Cl.
| | |
|---|---|
| *A61H 39/00* | (2006.01) |
| *A61H 39/08* | (2006.01) |
| *A61K 39/00* | (2006.01) |
| *A61K 39/35* | (2006.01) |
| *A61K 49/00* | (2006.01) |
| *A61B 5/00* | (2006.01) |
| *A61H 39/02* | (2006.01) |

(52) U.S. Cl.
CPC ............ *A61H 39/086* (2013.01); *A61B 5/411* (2013.01); *A61H 39/002* (2013.01); *A61H 39/08* (2013.01); *A61K 39/35* (2013.01); *A61K 49/0006* (2013.01); *A61H 39/02* (2013.01); *A61H 2205/027* (2013.01); *A61K 2039/575* (2013.01)

(58) Field of Classification Search
CPC ........ A61H 39/00; A61H 39/08; A61K 49/00; A61B 5/00
See application file for complete search history.

(56) References Cited

U.S. PATENT DOCUMENTS

| | | |
|---|---|---|
| 2005/0101031 A1 | 5/2005 | Hiller et al. |
| 2008/0249439 A1 | 10/2008 | Tracey et al. |
| 2010/0004703 A1 | 1/2010 | Smith |
| 2010/0137896 A1 | 6/2010 | Mukhina et al. |

OTHER PUBLICATIONS

The PCT Search Report and Written Opinion dated Feb. 16, 2016 for PCT application No. PCT/US2015/064685, 10 pages.
Xue, et al., "Effect of Accupuncture in the Treatment of Seasonal Allergic Rhinitis: A Randomized Controlled Clinical Trial", The American Journal of Chinese Medicine, 2002, vol. 30, No. 1, pp. 1-11.
Bourdiol, Rene. Elements of Auriculotherapy. 1982. pp. 138-139 and 214-215.
Huang, Li-Chun. Auriculotherapy: Diagnosis and Treatment. Longevity Press. 1996. pp. 64-65.
Nogier, Paul, et al. The Man in the Ear. Maisonneuve, Sainte-Ruffine, France. 1985. pp. 32-33.
Oleson, Terry. Auriculotherapy manual: Chinese and Western systems of ear acupuncture. Elsevier Health Sciences, 2014. p. 153.
Rubach, Axel. Principles of Ear Acupuncture: Microsystem of the Auricle. Thieme, Stuttgart, Germany. 2001. pp. 66-67, 185, and 218.
Strittmatter, Beate. Ear Acupunture: A precise pocket atlas based on the works of Nogier/Bahr. 2003. pp. 200-201 and 296-297.
Gori, et al. "Ear Acupuncture in European Traditional Medicine" 2007, eCam vol. 4 (S1), pp. 13-16.
Alonso, A., et al, Allergy, histamine 1 receptor blockers, and the risk of multiple sclerosis, Department of Epidemiology, Harvard School of Public Health, AAN Enterprises, Feb. 2006 (4 pages).
Associated Autoimmune Diseases, GIG Education Bulletin, Jun. 2014, (2 pages).
The Canadian Office Action dated May 1, 2018 for Canadian Patent Application No. 2968681, a counterpart foreign application of U.S. Appl. No. 15/531,969, 4 pages.
The Halpin Foundation: Allergic and Autoimmune Diseases Connected, Medical News Today Jun. 12, 2013 (2 pages).
Hidaka, Y., et al, Recurrence of thyrotoxicosis after atack of allergic rhinitis in patients with Graves' disease, Endocrine Society, PubMed, NCBI, Dec. 1993 (1 page).
NIH scientists find link between allergic and autoimmune diseases in mouse study, National institute of Health, https://www.nih.gov/news-events/news-releases/nih-scientists-find-link-between-allergic-autoimmune-diseases-mouse-study (4 pages).
Allergy and Autoimmune Disorders, OurMed.org, retrieved from Wikipedia.com, Jun. 5, 2018 (4 pages).
Sanjuan, M., et al, Role of IgE in autoimmunity, J. Allergy Clin. Immunol., Jun. 2016 (pp. 1651-1661).
Valenta, R., et al, Linking allergy to autoimmune disease, PubMed, NCBI, Feb. 21, 2009 (1 page).
Walker, M., et al, New Insights into the Role of Mast Cells in Autoimmunity: Evidence for a Common Mechanism of Action?, Department of Microbiology and Immunology, Norhtwestern University Feinberg School of Medicine, Feb. 25, 2011 (19 pages).

*Primary Examiner* — Zohreh A Fay
(74) *Attorney, Agent, or Firm* — Lee & Hayes, P.C.

(57) ABSTRACT

The present disclosure provides a method of treating allergies and autoimmune diseases using microsystem acupuncture. Methods provided herein for treating allergies and autoimmune diseases using microsystem acupuncture involving a novel allergy zone. In embodiments, the method includes identifying an allergy zone (AZ) (Soliman Allergy Zone (SAZ)) (FIG. 1 A) in an acupuncture microsystem of a subject in need of treatment and treating the zone to treat the allergy or autoimmune disease. In embodiments, treating the zone includes introducing an acupuncture needle in the zone. In particular embodiments, the method includes identifying one or more active points in the liver projection site of the AZ and treating the active point or points.

14 Claims, 12 Drawing Sheets

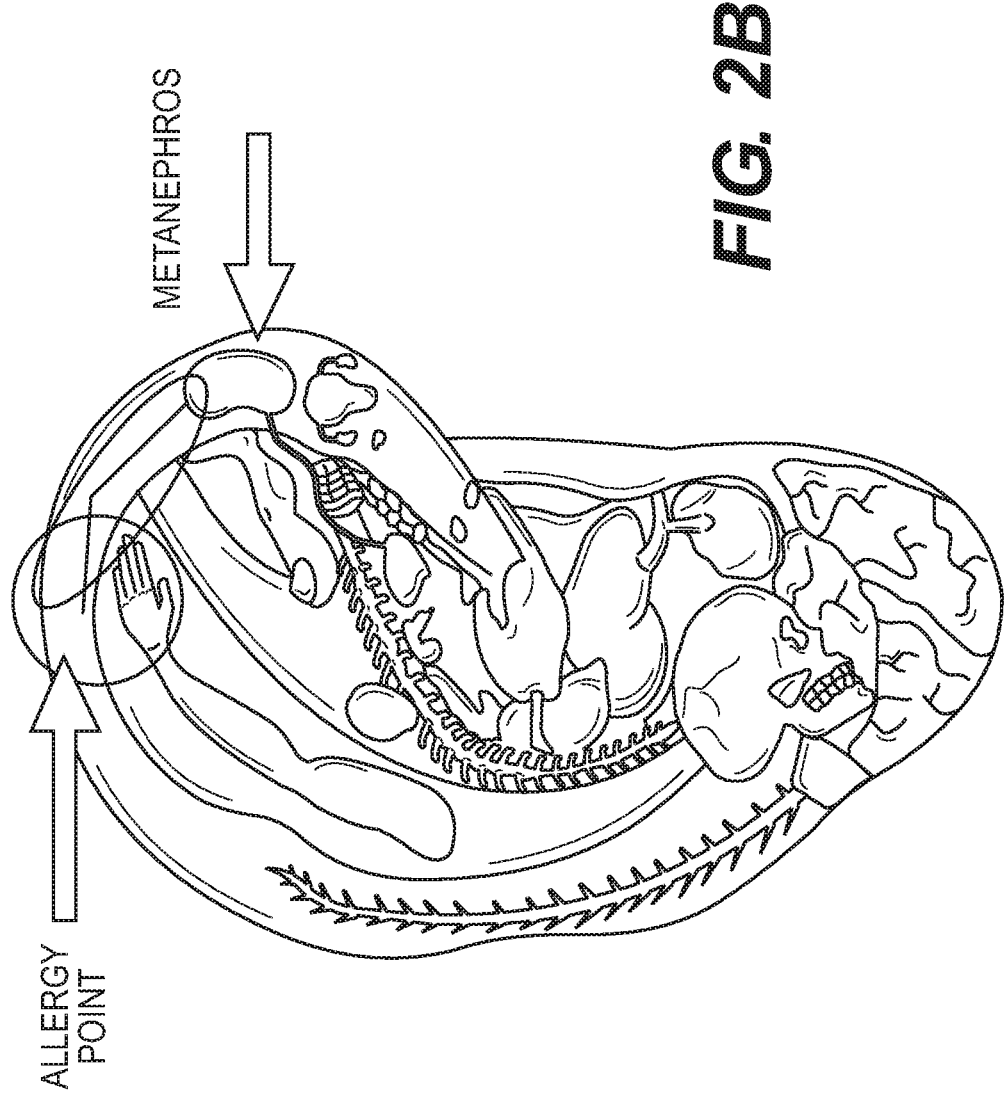

TREATMENT OF ALLERGIES AND AUTOIMMUNE DISEASES

CROSS REFERENCE TO RELATED APPLICATIONS

This application is the U.S. National Stage under 35 U.S.C 371 of International Application No. PCT/US2015/64685 filed Dec. 9, 2015, which claims the benefit of priority of U.S. Provisional Application 62/089,303, filed on Dec. 9, 2014, both of which are incorporated herein by reference in their entirety.

FIELD

The present disclosure relates to the treatment of immune disorders, such as allergies and autoimmune diseases, using acupuncture.

BACKGROUND

The function of the immune system is to protect an individual against infections and diseases. An immune response is how the immune system defends against any substance that appears to be foreign and harmful, such as parasites, bacteria, and viruses. Antigens are molecules that stimulate an immune response. Antigens are contained within cells or on the surface of cells, such as bacteria, or are a part of a virus. Normally, the immune system reacts only to antigens from foreign or dangerous substance. However, sometimes the immune system goes awry causing disorders and conditions, such as allergies and autoimmune diseases.

Allergies are disorders resulting from an active immune response reacting to a harmless allergen such as dust, pollens, pet dander, or food. An allergic reaction occurs when the immune system reacts by producing large quantities of antibodies to attack the allergen. Allergic conditions are a major medical problem all over the world. Allergies are among the most difficult medical conditions to treat and eliminate. Allergies tend to critically influence the quality of life in affected patients, with both physical and economic repercussions. In North America alone allergies afflict about 50 million individuals and cost patients and insurance companies up to 10 billion dollars annually. Allergies are known to develop at any age and can be triggered by anything under the sun including the sun itself.

Autoimmune diseases arise from over stimulation of the immune system against substances and tissues normally present in the body. In other words, the immune system interprets the body's own cells or tissues as foreign and produce autoantibodies or immune cells that attack the cells or tissues of the body, which results in inflammation and tissue damage. As many as five percent of Americans suffer from some form of autoimmune disease, which includes lupus, rheumatoid arthritis, multiple sclerosis, Graves' disease, myasthenia gravis, and insulin-dependent diabetes mellitus.

From the perspective of immune function, allergies are the initial phase of immune over stimulation that are triggered from outside of the body, whereas autoimmune reactions are a late phase of chronic immune over stimulation that occurs within the body causing damage to tissue, glands, and organs. Thus, if the root source of these allergies are not found and corrected, then the allergies can eventually become chronic immune over stimulation and can transform into autoimmune disease.

Traditional western medical treatment for allergies includes; antihistamines and steroids treatment both of which offer only temporary relief from the symptoms for only few hours. Allergy shots are another method of treatment for allergic reactions. Allergy shots are usually performed over many years on a weekly bases with only minor improvements. Since allergy shots introduce to the body the same substances that the patient is allergic to, the possibility of an anaphylactic shock is authentic. This is a catastrophic reaction that can lead to a patient's death. To prevent this complication, patients receiving allergy shots always carry epinephrine injections.

Traditional western medical treatments for allergy are largely ineffective and of long duration, in addition they financially burden the population and the health care system.

Acupuncture techniques have been used to help safely attenuate allergy symptoms, but they are unable to completely eliminate them. One prior acupuncture system for the treatment of allergies used the ear (auricular acupuncture microsystem) as the lone treatment site for allergic reactions. In 1961 Paul Nogier of France introduced the auricular acupuncture microsystem with its "inverted fetus" presentation. Dr. Nogier eventually identified a specific point on the ear that he designated as the "Allergy point". Nogier's allergy point is located at the most posterior part of the projection site of the metanephros. The metanephros is the embryologic remnants of the kidney tissue after fetal development. Attempts to use this particular acupuncture point to treat allergic reactions by many practitioners failed to yield any good results. Allergies were either slightly or only temporarily relieved or simply never responded to the treatment.

In general, there is a great need to address such an elusive medical problem and eliminate the high cost to patient, insurance companies and the health care system.

SUMMARY

Acupuncturists practicing allergy treatment are basically following treatments advised for many years by acupuncture books. Though the results are generally unsatisfactory the overall outcome was relatively better and much safer than what western medicine can offer for the same problem. Obviously, this was accepted as a fact and nobody investigated the possibility of additional zones of treatment for allergy problems.

Methods provided herein for treating allergies and autoimmune diseases using microsystem acupuncture involving a novel allergy zone. In embodiments, the method includes identifying an allergy zone (AZ) (Soliman Allergy Zone (SAZ)) (FIG. 1A) in an acupuncture microsystem of a subject in need of treatment and treating the zone to treat the allergy or autoimmune disease. In embodiments, treating the zone includes introducing an acupuncture needle in the zone. In particular embodiments, the method includes identifying one or more active points in the liver projection site of the AZ and treating the active point or points.

Methods for identifying allergens or substances that trigger an allergic reaction in a subject are provided herein. In embodiments, the method identifies the allergen or substance that trigger an allergic reaction by detecting an active point or points in the projection site of the liver of the AZ of an acupuncture microsystem.

The benefits of the methods provided herein include: simplicity of the treatment; minimum duration of treatment; lack of side effects, complications, and anaphylactic reactions; lack of need to take medication repeatedly; and no repeated frequent visits to medical doctors.

BRIEF DESCRIPTION OF THE DRAWINGS

FIGS. 2A-2C show the allergy zone on the ear reported by Dr. Paul Nogier. (A) Inverted Fetus Concept. (B and C) Maps showing the Allergy Point (arrow) and the projection sites of different parts of the body on the ear defined by Dr. Paul Nogier.

FIGS. 4A-4C show muscle testing using the O-ring test.

DETAILED DESCRIPTION

Acupuncture, a form of alternative medicine, is based on the general premise that there are patterns of energy flow (qi) through the body that are essential for health. Traditional acupuncture involves the belief that qi circulates within the body in lines called meridians. Disruptions in the flow of qi are the cause of diseases. Acupuncture corrects the imbalances of flow at identifiable points close to the skin by stimulation of specific acupuncture points using thin needles.

The majority of the people who seek out acupuncture do so for musculoskeletal problems, including lower back pain, shoulder stiffness, and knee pain. Though commonly used for pain relief, acupuncture is also used to treat a wide range of conditions.

Microsystem acupuncture is a form of acupuncture that is based on the belief that the organs and parts of the body are reflected in a small defined area of its body. A microsystem is situated on parts of the body, such as the ear, scalp, abdomen, hand, foot, face, tongue, eye, or oral cavity. A microsystem is like a map of the body, and each microsystem contains acupuncture points and zonal representation of different organs and structures that correlate to and interrelates with a particular organ or function. It has been shown that conditions of the body, wherever they may be, can be treated by stimulating the corresponding acupuncture points or zonal representation in one of the microsystem using devices, such as needles. In other words, the practice of microsystem acupuncture can involve stimulating well-defined areas of the body that reflect the body as a whole, both structurally and functionally in a topographic manner, in order to reflexively regulate corresponding body structures and systems for the treatment and prevention of disease and maintenance of health. Stimulating the well-defined area can involve inserting needles in that area.

Figure 1A:
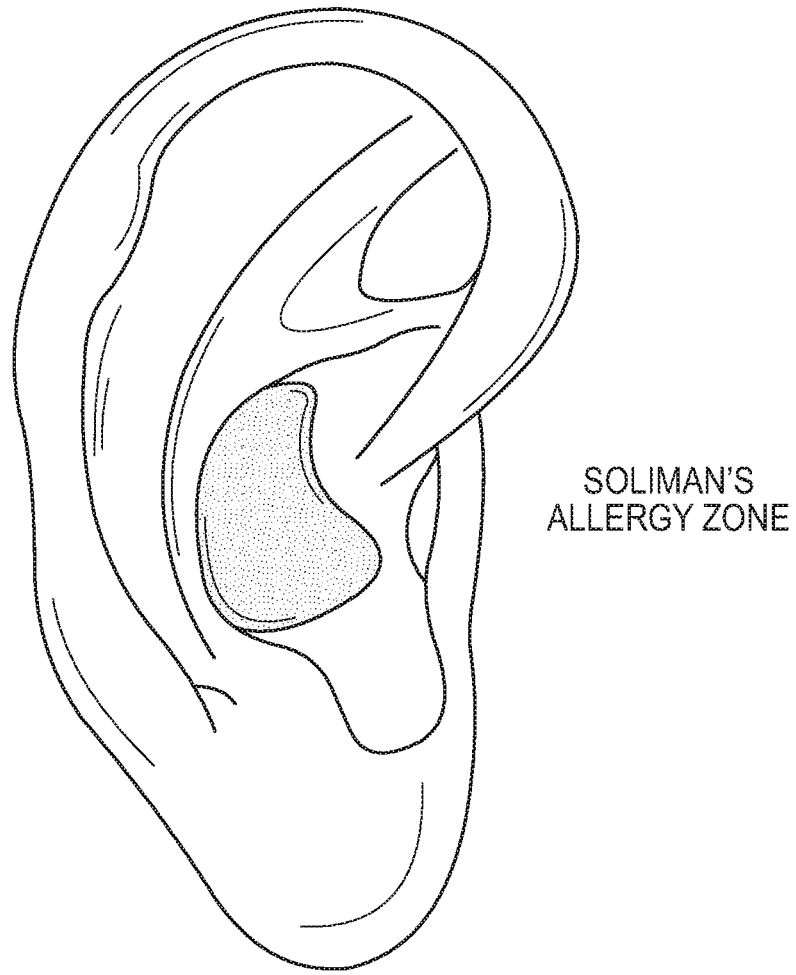
FIGS. 1A and 1B show (A) the newly discovered allergy zone (AZ), also known as Soliman's Allergy Zone (SAZ) and (B) a map of the organs of the body projected on the ear including the newly discovered allergy zone (AZ).
Figure 1B:
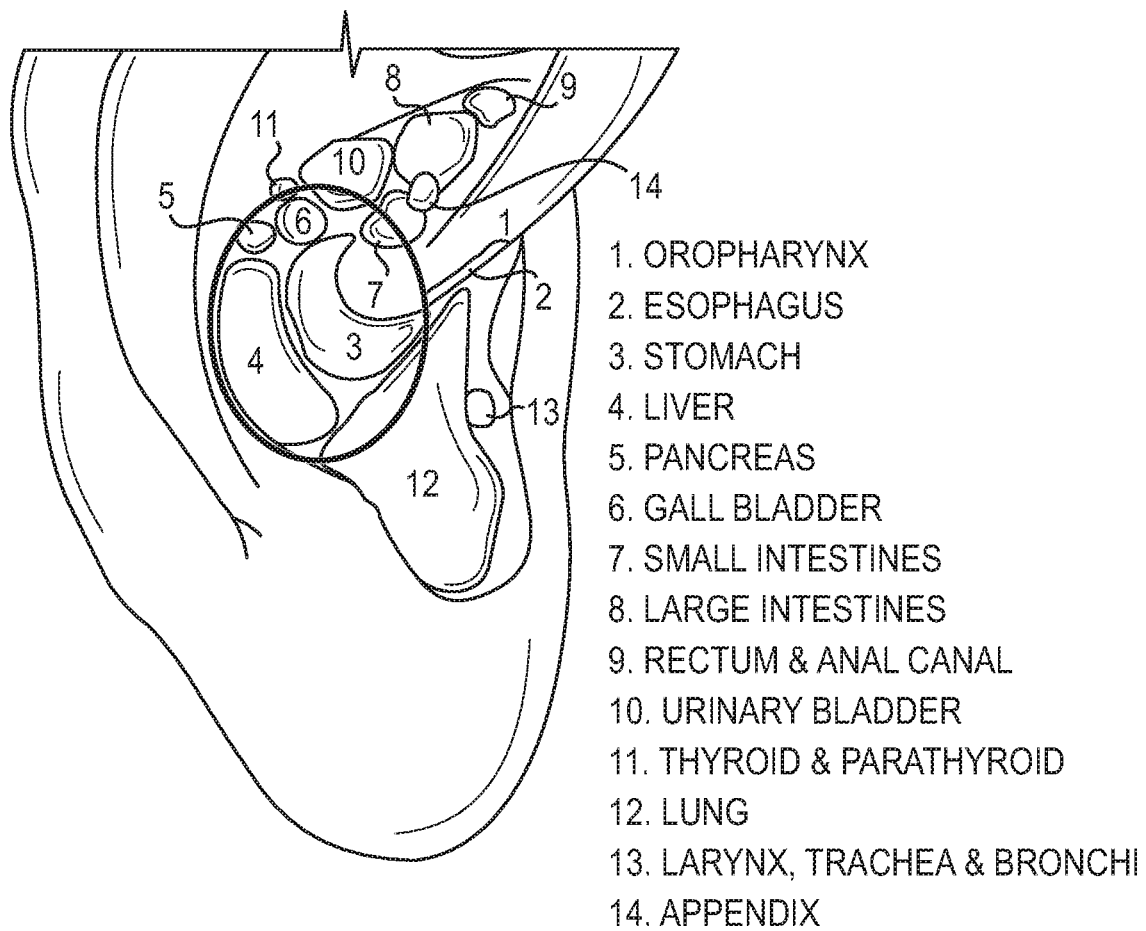
Figure 2A:
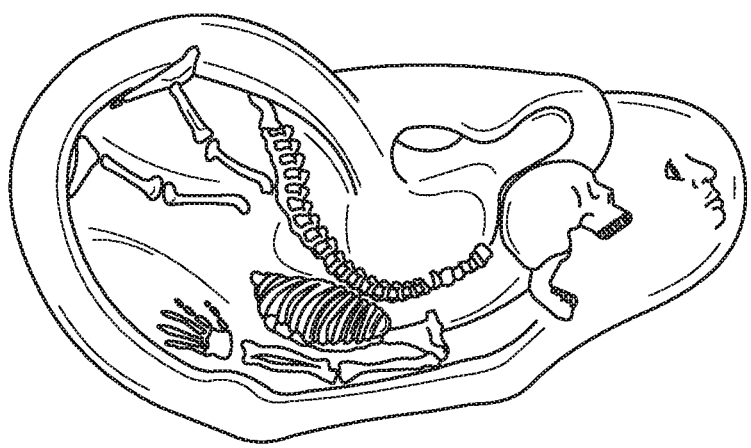
Figure 2A:
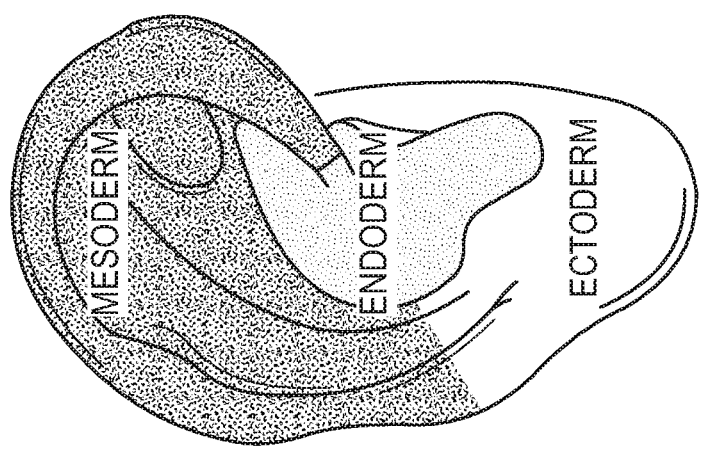
Figure 2A:
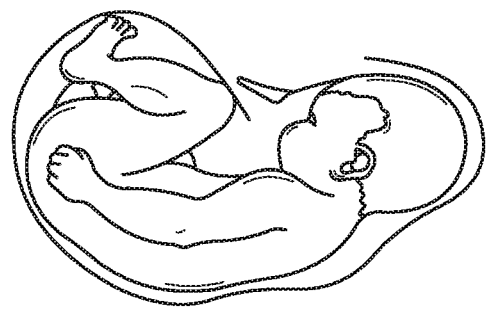
Figure 2C:
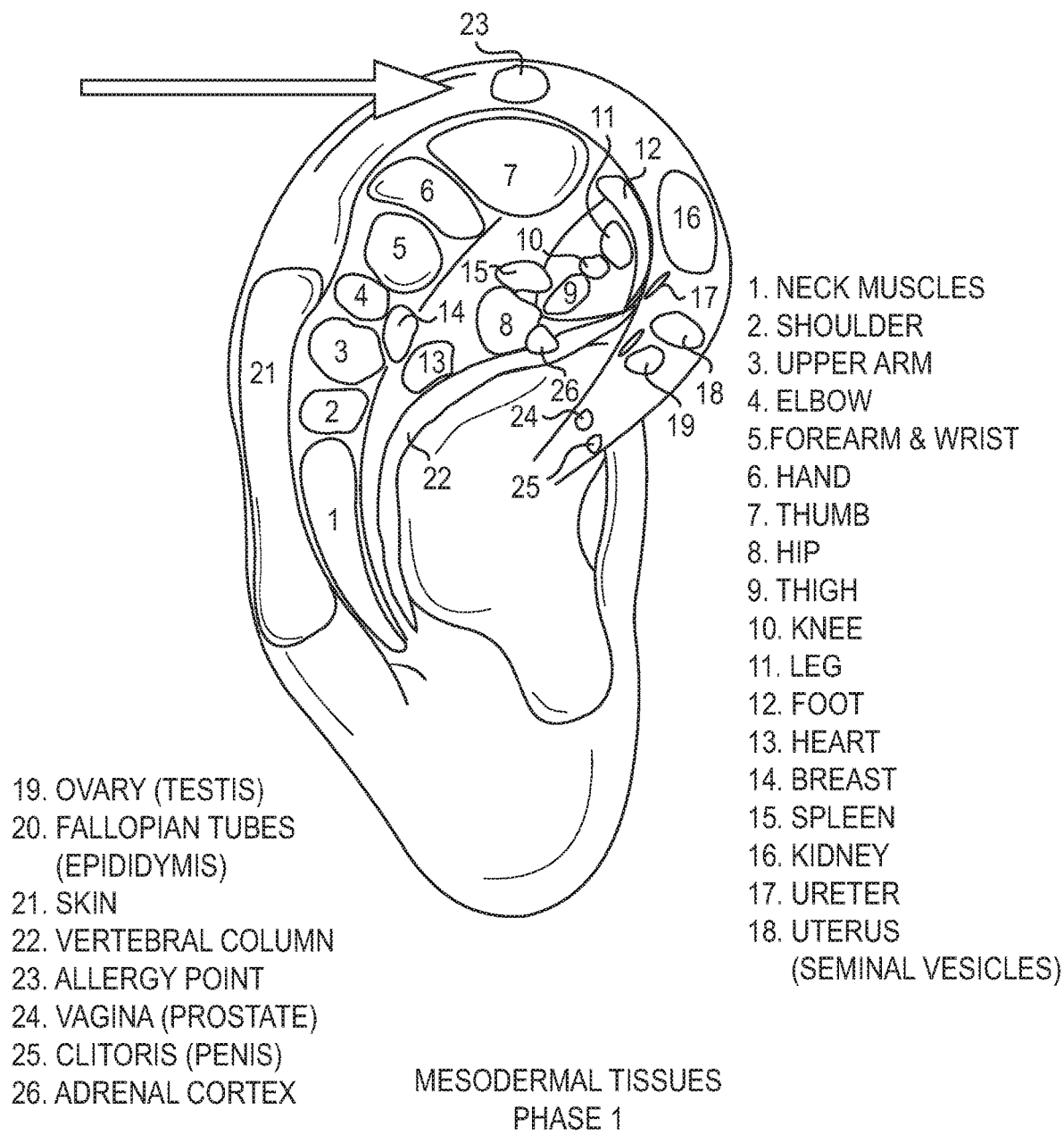
Figure 3A:
FIGS. 3A-3C show muscle testing using the arm strength test.
Figure 3B:
Figure 3C:
Figure 4B:
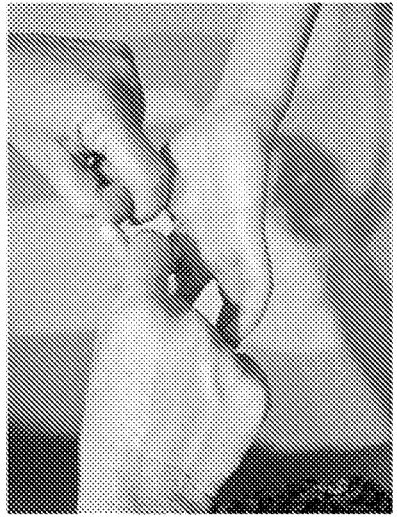
Figure 4A:
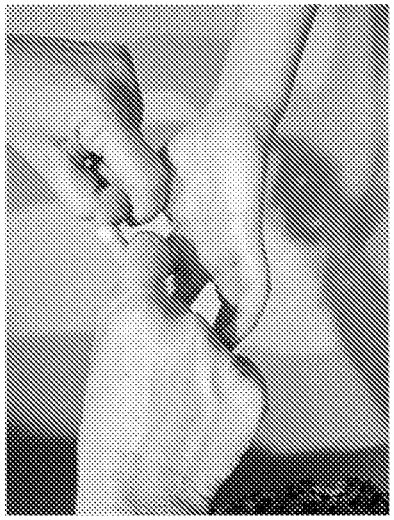
Figure 5B:
FIGS. 5A and 5B show detecting the electrically active point using a Pointer Plus (A) and introducing a needle in the electrically active point (B).
Figure 5A:

Auricular acupuncture or ear acupuncture is a form of microsystem acupuncture developed by Dr. Paul Nogier. In the 1950's, Dr. Nogier discovered the system of specific points on the auricle, which is also the first microsystem to be discovered. Dr. Nogier mapped the functional correspondence of the respective auricular points and zones based on the inverted fetus concept (FIG. 2A), when he observed the occurrence of scars on the ears of a patient who were successfully treated for sciatic pain by French lay practitioners. The auricular microsystem mapped by Dr. Nogier is very detailed though the specific points and zones are densely packed (FIG. 2B).

Auricular acupuncture is a treatment system based on the auricular points and auricular zones mapped by Dr. Nogier. The treatment normalizes the body's pain and dysfunction through stimulation of points on the ear. The resulting amelioration of pain and illness is believed to be through the reticular formation through the sympathetic and parasympathetic nervous systems.

In 1980, Drs. Richard J. Kroeuning and Terry D. Oleson conducted a double blind experimentally controlled research study at UCLA Pain Management Center, Department of Anesthesiology, at the UCLA School of Medicine. This study verified the scientific accuracy of auricular (ear) diagnosis. It was reported that a statistically significant level of 75% accuracy was achieved in diagnosing musculoskeletal pain problems in 40 pain patients. Specific areas of height and tenderness and increased electrical activity on the ear predicted specific areas of the body where some pain or dysfunction would be identified whereas the body free of pathology corresponded to non-active points on the ear. These points can be treated with needles, or without needles using electrical stimulation or small pellets or seeds applied with tape and pressed to stimulate the points.

Today, microsystem acupuncture using hands, feet, ear, etc. has been used to alleviate pain, improve vision, and treat anxiety and various eye conditions including glaucoma, macular degeneration, cataracts, and retinal detachment. Known microsystem acupuncture techniques, such as Dr. Nogier's auricular acupuncture, have also been used to treat allergies. However, these techniques only alleviate the symptoms temporarily and do not cure allergies.

Both allergies and autoimmune diseases result from a hyper or exaggerated immune response. Allergies, also known as allergic diseases, are caused by hypersensitivity of the immune system to something from the environment that is usually harmless to most people. Allergies are an initial phase of immune over stimulation that are triggered from outside of the body, whereas autoimmune reactions are a late phase of chronic immune over stimulation that occurs within the body causing damage to tissues, glands, and organs.

The immune system is responsible for recognizing and defending against foreign substances known as antigens. Allergens are particular antigens that produce an overly vigorous immune response to fight off a perceived threat that would otherwise be harmless to the body. In such an immune response, antibodies are over produced, and subsequent exposure causes an allergic reaction. Thus, when an allergen comes in contact with a subject predisposed to allergies, it triggers an immune response and the production of antibodies. The allergen antibodies migrate to the mast cells lining the nose, eyes, and lungs. When an allergen drifts into the nose more than once, the mast cells release histamines that irritate and inflame the moist membranes lining the nose and produce the symptoms of an allergic reaction, such as uticaria (hives, scratchy throat, itching, sneezing, and watery eyes. Allergens can provoke unpleasant reactions ranging from irritating sniffles of hay fever to a life-threatening circulatory collapse that occurs in systemic anaphylaxis.

Sources of allergens include animal products, plants, food, insect stings, drugs, fungal spores, and microorganisms. Examples of allergens from animal products include fur, dander, cockroach calyx, wool, dust mite excretion, and fel d 1 (a protein produced in cat saliva and sebaceous glands). Examples of allergens from plant include plant pollens from grass such as ryegrass; weeds such as ragweed, nettle, sorrel; and trees such as birch, alder, hazel, oak, elm, and maple. Also, urushiol is a resin produced by poison ivy and poison oak that is an allergen which causes skin rash. Examples of food allergens include peanuts, tree nuts such as pecans and almonds, eggs, milk, shellfish, fish, wheat and their derivative, soy and their derivatives. Examples of allergens from insect stings include bee sting, wasp sting, and mosquito stings. Examples of drug allergens include penicillin, sulfonamides, quinidine, phenylbutazone, thiouracils, methyldopa, hydantoins, and salicytates. Example of fungal allergens include basidiospores such as Ganoderma; mushroom spores; allergens from the aspergillus and alternaria-penicillin families; and cladosporium spores. Examples of microorganisms that can cause an allergic reaction include viruses and bacteria. Other allergens include latex, metal, wood, chemicals, cosmetics, dyes, vaccines, hormones, vegetables, fruits, sugars, animals and essentially anything under the sun, including the sun itself. Another example of an allergen can be semen. Infertility can be caused by sensitization of a woman to her partner's semen. This is a true allergy that may prevent conception in the normal way leading to increased medical expenses.

In a normal immune response, immunoglobulins, such as IgM, IgG, IgA, IgD, and IgE, which function as antibodies, and other immune cells defend against the foreign invaders and eliminate them. The immunoglobulins bind to specific antigens, and leukocytes are recruited to destroy the antigens.

Allergic reactions are classified into four different types based on the immune system's response to the allergen. Type I allergic reactions involve IgE, which is specific for a particular drug, antigen, or other allergen that triggers an allergic reaction. In Type I allergic reactions, the allergen binds to the immunoglobulin on immune cells such as basophils and mast cells and triggers the release of chemicals that cause inflammation in the body within 30 minutes of exposure. These chemicals cause allergy symptoms such as uticaria, runny nose, watery eyes, sneezing, wheezing, and itching. Type II allergic reactions are cytotoxic reaction, involving the destruction of host cells by an antigen specific antibody, such as IgG or IgM. Type II allergic reactions usually occur within five to twelve hours after exposure to allergens such as penicillin, quinidine, phenylbutazone, thiouracils, sulfonamides, or methyldopa. Type III allergic reactions involve the formation of an antigen-antibody immune complex, which deposits on blood vessel walls and activates cell components known as complements. Type III allergic reactions cause symptoms such as fever, swelling, skin rash, and enlargement of the lymph nodes in about three to eight hours after exposure to allergens, including penicillins, sulfonamides, intravenous contrast media, and hydantoins. Type IV allergic reactions involve delayed cell mediated reactions. Type IV allergic reactions occur when antigens on the allergen release inflammatory mediators in 24 to 48 hours and are seen with graft rejection, latex contact dermatitis, and tuberculin reactions.

In Type I allergic reaction, the IgE antibodies bind to mast cells and other similar cells. Mast cells play an important role in the immune and neuroimmune systems. Their functions include innate immunity, defense mechanisms against parasitic infestations, immunomodulation, and tissue repair. Mast cells are found in major organs of the human body, especially those that are vascular, such as the liver, and those that are in direct contact with the external environment including the skin, respiratory tract, and digestive tract. Mast cells accumulate in sites where foreign material attempts host invasion, suggesting that they are one of the first cell populations to initiate defense mechanisms. Mast cells contain granule rich in histamine and heparin. Upon activation, mast cells degranulate releasing histamine.

Treatment of allergies in western medicine involves administering antihistamines, steroids, epinephrine, and allergy shots. Omalizumab (Xolair), which interferes with the body's ability to utilize IgE, was approved in March 2014 in the European Union, U.S., and ten other countries for the treatment of chronic spontaneous uticaria (CSU), which cannot be treated with H1-antihistamines. However, CSU is not an allergic disease. Omalizumab is currently undergoing clinical trials for various allergic diseases and some non-allergic diseases, such as skin diseases. Oral immunotherapy is another experimental treatment. In oral immunotherapy, small doses of food allergens are swallowed or placed sublingually, and the doses of the food allergens are gradually increased. Both experimental treatments require a considerably long treatment period with unproven effectiveness.

Autoimmune disease are caused by the immune system, in response to an unknown trigger, producing antibodies that attack the body's own tissues instead of fighting infections. An autoimmune disease can affect one or many different types of body tissue. It can also cause abnormal organ growth and changes in organ function. The most common organs and tissues affected include joints, muscles, skin, red blood cells, blood vessels, connective tissues, and endocrine glands. Some common symptoms of autoimmune disease include fatigue, fever, and general malaise. Symptoms worsen during flare-ups and lessen during remission.

There are as many as 80 types of autoimmune diseases. Some of the more common autoimmune disorders include Graves disease, rheumatoid arthritis, Hashimoto thyroiditis, type I diabetes, systemic lupus erythematosus (lupus), inflammatory bowel disease (IBD), Crohn's Colitis, multiple sclerosis, Guillain-Barre syndrome, psoriasis, Myasthenia Gravis, vasculitis, Addison disease, polymyositis, Sjögren syndrome, progressive systemic sclerosis, many cases of glomerulonephritis (inflammation of the kidneys), and some cases of infertility.

Autoimmune diseases are chronic conditions with no cure. Thus, treatment involves attempts to control the process of the disease to alleviate symptoms, especially during flare-ups. Medical interventions include hormone replacement therapy, blood transfusions (if blood is affected), anti-inflammatory medication (if joints are affected), pain medication, immunosuppressive medication, and physical therapy. Some alternative therapies that have provided relief, but not cure, for some people include herbs, chiropractic therapy, acupuncture, and hypnosis.

Although the causes of autoimmune diseases are unknown, there is evidence that autoimmune diseases is caused by an allergy to microorganisms, such as bacteria or virus; drugs; chemical irritants; and environment irritants. Viral infection triggers central nervous system autoimmunity via activation of CD8+ T cells expressing dual T cell antigen receptors (TCRs). (Qingyong Ji, et al., Nature immunology, 2010 11, 628-634.) Moreover, similar to the response to allergic reactions, autoimmune diseases involve hypersensitivity reactions. Further, it has been reported that mast cell activation is followed by synthesis of chemokines and cytokines. Cytokine and chemokine secretion contributes to chronic inflammation.

The present disclosure provides novel methods for treating allergies and autoimmune diseases based on microsystem acupuncture. Although various acupuncture techniques have been used to treat allergies, those techniques included body acupuncture treatment and all of these treatments completely excluded the ear's acupuncture microsystem. In contrast to the previous allergy treatments involving body acupuncture, the present disclosure provides a method that solely uses the ear for the treatment of allergies and autoimmune diseases. Moreover, the methods disclosed herein use the liver's projection site on a microsystem for the treatment of allergies and autoimmune diseases.

Liver appears to be responsible for the emergence of allergies in transplant patients. For example, new onset post transplantation food allergies following liver transplantation are common. New onset post transplantation food allergies following kidney transplantation are uncommon. Additionally, it has been reported that immunomodulatory properties of immunosuppressive drugs cannot be primarily blamed for the allergies.

As mentioned above, Dr. Nogier introduced the auricular microsystem acupuncture in the 1950's. Dr. Nogier eventually identified a specific point on the ear that he designated as the "Allergy point" (FIG. 2B). Dr. Nogier's allergy point is located at the most posterior part of the projection site of the metanephros, the embryologic remnants of the kidney tissue after fetal development (FIG. 2B). The metanephros' projection onto the ear starts at the site of the Kidney's projection and proceeds posteriorly to end at the level where the upper crus of the antihelix intersects with the body of the helix. Along its entire course, the point is projected onto the hidden surface of the body of the helix. Upon folding the auricle along its vertical axis, Nogier's Allergy point can be identified at the highest point of the ear. Attempts to use this particular acupuncture point to treat allergic reactions by many practitioners failed to yield any good results. Allergies were either slightly or only temporarily relieved or simply never responded to the treatment. Practically, this point was successful in only attenuating some of symptoms related to some environmental allergies but completely failed to eliminate them. It was also found to be completely ineffective in addressing allergies related to food, drugs, and contact allergies.

The present disclosure provides a novel allergy zone (AZ), also called the Soliman's Allergy Zone (SAZ), for treating allergies and autoimmune diseases using the acupuncture microsystem. In embodiments, the AZ is located on an acupuncture microsystem. In other embodiments, the AZ includes the projection area of the liver and the stomach on an acupuncture microsystem. In particular embodiments, the acupuncture microsystem includes the ear, hand, foot, face, scalp, tongue, and oral cavity.

As shown in FIGS. 1A, 1B and 2A-2C, the newly discovered AZ of the ear is different from the area designated as the allergy point by Dr. Paul Nogier on the ear. This newly discovered AZ is completely unrecognized for the purpose of allergy treatment. No literature or acupuncture books ever mentioned this zone as being related to addressing allergic reactions.

Methods provided herein include using the newly discovered AZ for treating allergies and autoimmune diseases. In embodiments, the projection site of the liver in the AZ is identified and used to treat allergies and autoimmune diseases. In other embodiments, the projection site of the liver in the AZ on the ear is used by the methods provided herein.

As a single organ, the liver is located on the right side of the body. Though the projection site of the liver on the ear can be detected on both ears, the projection site on the right ear is more pronounced. In embodiments, the methods disclosed herein use the right ear for treating allergy and autoimmune diseases. In particular embodiments, the right ear is used in the methods of treatments provided herein, unless it is deformed or missing.

Methods provided herein also include identifying one or more active points in the AZ of a microsystem acupuncture for treating allergies and autoimmune diseases. Contrary to Nogier's allergy approach, methods provided herein do not treat allergies and autoimmune diseases by treating a universal zone. Instead, each allergen is expected to have a specific corresponding active point or points within the AZ.

Organs are projected onto an acupuncture microsystem as zones not as points. These zones of projection have fluctuating boundaries reflecting the energetics of the corresponding organs. Boundaries are ever-changing, and projection sites are not limited to any certain configurations. Projections sites can easily overlap without loosing their energetic uniqueness or specific frequencies.

The energetic disturbances associated with an allergen create activity within the corresponding zone. Energetic activity converges to form a specific electrically active point within the zone. Active points are not fixed and could be identified at different sites within the projection sites of any organ or structure with different examination. This reflects the ever-changing dynamics of the actual organs and structures. Moreover, more than one active point for an allergen can be encountered.

Identifying one or more active points in the AZ of a microsystem acupuncture includes exposing a suspected allergen to a subject. The allergen can be the actual substance, a suspected substance, or a homeopathic preparation. The homeopathic preparation can have a potency of about 6 times to about 30 times the potency of the actual suspected substance.

The allergen induces a state of bio-energetic stress in the subject, and the bio-energetic stress becomes more evident in the organ or structure involved in the allergic reaction. Thus, exposing a subject to a substance will create a temporary state of bio-energetic stress if the patient is allergic or sensitive to the substance, which is due to resonance with electromagnetic frequency of the substance (allergen). The bio-energetic stress is reflected on the projection site of the organ in the AZ of an acupuncture microsystem. The energetic disturbance will then converge to form one or more points that become electrically active or exceptionally tender within the projection site of the organ in the AZ.

This point reflects the energetic imbalance related to the allergic reaction, while the subject is exposed to the allergen. The energetic system will continue to display the bio-energetic stress associated with the allergen. This point is the area to be addressed to initiate an energetic response to help reverse the reaction to the allergen in question. This is the point sought to treat allergies or autoimmune diseases of a subject.

In embodiments, as the organ involved in the allergic reactions, the liver's bio-energetic stress will be reflected on its somatotopic projection on its auricular projection that becomes energetically disturbed. The energetic disturbance will then converge to form one or more points that are electrically active or exceptionally tender within the liver's projection site.

The active point or points in the AZ can be detected using any microsystem acupuncture device such as a point finder or locator. The point finder is positioned close to the acupuncture microsystem, for example the ear. On detecting the active point, the point finder produces an audible, visual, tactile, or combination indication. Examples of such devices include the Pointer Plus, and Net 3000 or similar devices.

Once one or more active points in the AZ are identified, the one or more active points are treated. The active point can be treated by stimulation. Treatment of the active point by stimulation includes treatment with a needle or without a needle using electrical stimulation or small pellets or seeds applied with tape and pressed to stimulate the point or points. In embodiments, an acupuncture needle is used and is introduced at the active point or points. Methods provided herein also include making an indentation or a mark prior to treating the active point. Moreover, a temporary needle can be introduced at the active point which enables re-evaluation of the electrically active point to fine tune the position of the needle in relations to the active point. Introducing a needle includes inserting a needle in the active point.

Treatment is to remain at the active point for a period of time, for example at least one week, two weeks, or three weeks. In embodiments, the acupuncture needle remains inserted at the active point for three weeks. The needle is removed after the period of treatment.

Examples of acupuncture needles that can be used include ASP, spinex, and any kind of small acupuncture needles that will remain in place over the period of time of treatment without interfering with the subject's daily routine.

Methods disclosed herein include treating subjects (humans, veterinary animals (dogs, cats, reptiles, birds, etc.), livestock (horses, cattle, goats, pigs, chickens, etc.), and research animals (monkeys, rats, mice, fish, etc.). Subjects in need of a treatment (in need thereof) are subjects having allergies or autoimmune disease.

Methods disclosed herein also include evaluating the subject's response to a suspected allergen prior to identifying the electrically active point, in order to confirm that the subject is allergic to the suspected allergen. Methods for evaluating a subject's response to a suspected allergen include muscle testing and techniques of auricular medicine.

Examples of muscle strength testing include the arm strength test, O-ring test, hand grip test, and other known tests. Any muscle of the subject can be tested before or after applying the suspected allergen. Knowing exactly what the muscle is used for can be useful for testing the strength of the muscle. By performing the muscle strength test, the muscle strength of the subject is defined and recorded prior to exposing the subject to the suspected allergen. The subject is then exposed to the allergen, which includes placing the suspected allergen on the hand or the forearm of the individual being treated. Allergens used are either the actual substances causing the allergies or a homeopathic preparation of the allergen in the potency of about 6 times to about 30 times of the actual substance. Muscle testing is then repeated following the placement of the allergen on the subject. Weakness of the muscles of the arm or the finger confirms the subject's susceptibility to the allergen.

Techniques of auricular medicine include pulse analysis methods which include observing vascular autonomic signal (VAS) and identifying changes in the ear's energy field known as the auricular bio-energetic field (BEF). The auricular bio-energetic field is a field of energy that is projected by the ear beyond its physical presence. Since the ear is a whole acupuncture microsystem, it is capable of projecting the energetic status of every single organ and structure in the body. The bio-energetic field of the ear can be identified using the three phase filter also known as a three color filter (tricolor filter). The three phase filter is a filter that has three specific color frequencies that resonate with the three phases of any pathology, such as acute, chronic, and chronic degenerative. By approaching the filter perpendicular to the ear from a distance, the position of the auricular bio-energetic field could be determined by a sudden change of the pulse quality which becomes stronger and more vibrant when the three color filter hits the auricular bio-energetic field. In this case, the placement of the substance in question on the individual's arm will evoke and energetic stress if the individual is allergic or sensitive to that substance. This in turn will result in expansion of the auricular bio-energetic field as a result of the stress of the liver organ that deals with the allergy and the sensitivity to any allergen. Reevaluating the auricular bio-energetic field with the method mentioned above will identify its border to be beyond the original site as indication of energetic stress.

The VAS also known as the vascular autonomic signal is a change in the pulse quality when the tricolor filter comes in contact with the auricular bio-energetic field. With the finger on any distal artery, such as the radial artery (which is the most used), the quality of the pulse is identified. As the tricolor filter comes in contact with the auricular bio-energetic field, it will create an energetic stress that is manifested by a change in the quality of the pulse. For a few arterial pulsations, the arterial pulse becomes stronger, fuller, and more vibrant reflecting the energetic stress felt by the individual.

Changes in the VAS can also help identify the position of the auricular BEF. The tricolor filter, can help with the identification of the position where the VAS changes which is the boundary of the auricular bio-energetic field.

Figure 6A:
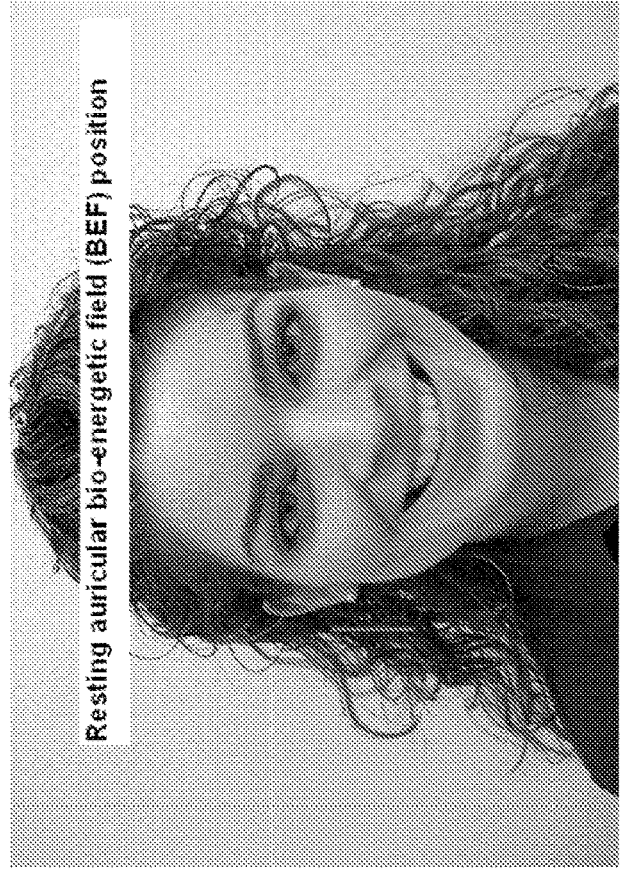
FIGS. 6A-6C show the auricular bio-energetic field (BEF) positions. (A) Resting position (pre-evaluation position). (B) BEF position after incorrect needling of the active point. (C) BEF position after correct needling of the active point.
Figure 6B:
Figure 6C:

As an example of using the techniques of auricular medicine, the BEF of the subject is first identified at resting position using the three phase filter; then the suspected allergen is applied to the arm of the subject (FIGS. 6A-6C). The auricular BEF is re-identified to determine whether there is a change. An expansion of the auricular BEF suggests that the patient is allergic or sensitive to the suspected allergen. In a similar manner, a change in the VAS can be identified in the presence of a suspected allergen to confirm that it is an allergen.

Methods provided herein also include re-evaluating the identified electrically active point in the AZ of an acupuncture microsystem in response to the suspected allergen. Re-evaluation seeks to fine tune the electrically active point for treatment by stimulation. The process can be repeated until there is no sign of distress or an absence of an expanded auricular BEF or of a change in VAS in the presence of the suspected allergen indicating that the correct active point has been localized.

Methods provided herein also includes identifying a substance suspected of triggering an allergic reaction in a subject.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments

1. A method of treating allergies, the method comprising,
(i) exposing a subject in need of treatment to a suspected allergen, (ii) identifying an allergy zone (AZ) (or Soliman's Allergy Zone (SAZ)) of an acupuncture microsystem of the subject in response to the allergen, and
(iii) treating the AZ.

2. The method of embodiment 1, wherein the method further comprises identifying a projection site of liver in the AZ and treating the projection site of the liver.

3. The method of any one of embodiments 1 or 2 wherein the method further comprises identifying one or more active points in the projection site of the liver and the one or more active points.

4. The method of any one of embodiments 1-3, wherein treating comprises stimulating the AZ or the one or more active points using a needle, using electrical stimulation, using small pellets, or using small seeds.

5. The method of any one of embodiments 1-4, wherein the needle is left in the one or more active points for at least one week.

6. The method of any one of embodiments 1-5, wherein the needle is left in the one or more active points for three weeks.

7. The method of any one of embodiments 1-6, wherein the acupuncture microsystem comprises ear, hand, face, scalp, foot, tongue, or eye.

8. The method of any one of embodiments 1-7, wherein the acupuncture microsystem comprises the ear.

9. The method of any one of embodiments 1-8, wherein the suspected allergen is the actual suspected allergen or a homeopathic preparation of the suspected allergen.

10. The method of any one of embodiments 1-9, wherein the suspected allergen is from an animal product, a plant, a food, an insect sting, a drugs, or a fungal spore.

11. The method of any one of embodiments 1-10, wherein the method further comprises evaluating the subject's sensitivity to the suspected allergen prior to step 1.

12. The method of any one of embodiments 1-11, wherein evaluating a subject's sensitivity to the suspected allergen comprises muscle testing or observing changes in vascular autonomic signal (VAS) or bio-energetic field (BEF).

13. The method of any one of embodiments 1-12, wherein the method further comprises evaluating a subject's sensitivity to the suspected allergen after step (iii).

14. The method of any one of embodiments 1-13, wherein evaluating a subject's sensitivity to the suspected allergen comprises muscle testing or observing changes in vascular autonomic signal (VAS) or bio-energetic field (BEF).

15. The method of any one of embodiments 1-14, wherein the allergen triggers the production of IgE immunoglobulins.

16. A method of treating autoimmune disease, the method comprising,
  (i) identifying an allergen causing the autoimmune disease in a subject,
  (ii) exposing the allergen to the subject,
  (iii) identifying an allergy zone (AZ) (or Soliman's Allergy Zone (SAZ)) of an acupuncture microsystem of the subject in response to the allergen, and
  (iv) treating the AZ.

17. The method of embodiment 16, wherein the allergen is a bacteria or a virus.

18. The method of embodiment 17, wherein the autoimmune disease is rheumatoid arthritis, system lupus, or Sjorgren's syndrome.

19. The method of any one of embodiments 16-18, wherein the method further comprises identifying a projection site of the liver in the AZ and treating the projection site of the liver.

20. The method of any one of embodiments 16-19, wherein the method further comprises identifying one or more active points in the projection site of the liver and the one or more active points.

21. The method of any one of embodiments 16-20, wherein treating comprises stimulating the AZ or the one or more active points using a needle, using electrical stimulation, using small pellets, or using small seeds.

22. The method of any one of embodiments 16-21, wherein the needle is left in the one or more active points for at least one week.

23. The method of any one of embodiments 16-22, wherein the needle is left in the one or more active points for three weeks.

24. The method of any one of embodiments 16-23, wherein the acupuncture microsystem comprises ear, hand, face, scalp, foot, tongue, or eye.

25. The method of any one of embodiments 16-24, wherein the acupuncture microsystem comprises the ear.

26. The method of any one of embodiments 16-25, wherein the suspected allergen is the actual suspected allergen or a homeopathic preparation of the suspected allergen.

27. The method of any one of embodiments 16-26, wherein the suspected allergen is from an animal product, a plant, a food, an insect sting, a drugs, or a fungal spore.

28. The method of any one of embodiments 16-27, wherein the method further comprises evaluating the subject's sensitivity to the suspected allergen prior to step 1.

29. The method of any one of embodiments 16-28, wherein evaluating a subject's sensitivity to the suspected allergen comprises muscle testing or observing changes in vascular autonomic signal (VAS) or bio-energetic field (BEF).

30. The method of any one of embodiments 16-29, wherein the method further comprises evaluating a subject's sensitivity to the suspected allergen after step (iii).

31. The method of any one of embodiments 16-30, wherein evaluating a subject's sensitivity to the suspected allergen comprises muscle testing or observing changes in vascular autonomic signal (VAS) or bio-energetic field (BEF).

32. A method of identifying an allergen, the method comprising,
  (i) exposing a subject to a substance suspected of triggering an allergic reaction in the subject,
  (ii) detecting one or more active points in a projection site of liver in the AZ in response to the allergen, thereby identifying the substance as an allergen.

33. The method of embodiment 32, wherein the substance is from an animal product, a plant, a food, an insect sting, a drugs, or a fungal spore.

34. The method of any one of embodiments 32 or 33, wherein the substance triggers the production of IgE immunoglobulins.

In contrast to known treatments, the methods described herein are characterized as follows:
  Providing permanent relief from any specific allergy with no known recurrence.
  Requiring only a single treatment.
  Requiring only a few minutes.
  Utilizing one tiny acupuncture needle.
  Side effects are almost negligible.
  Very minimal cost.

The term "active point" or "active site," as used herein refers to the electrically active point in the AZ, particularly in the projection site of the liver of an acupuncture microsystem. In response to an allergen, the bio-energetic stress converges to form an active point that is electrically active in the AZ of the acupuncture microsystem. The term "active point" or "active site" also includes one or more electrically active points or active sites.

The term "allergy zone (AZ)," also known as "Soliman's Allergy Zone (SAZ)," as used herein refers to a newly discovered area in an acupuncture microsystem that includes the projection site of the liver and overlapping the projection site of the stomach, upper one third of the projection site of the lung, and the projection sites of the pancreas, gallbladder, small intestines, thyroid and parathyroid glands, and part of the urinary bladder, and adjacent structures of an acupuncture microsystem. Anatomically, the AZ or SAZ, as an example, includes the posterior half of the concha overlying the root of the helix and upper third of the lower concha and posterior half of the upper concha. The newly discovered AZ is different from and does not include the allergy point previously defined by Dr. Paul Nogier.

The term "autoimmune disease," as used herein includes autoimmune conditions.

The term "allergic reaction or response" or "sensitivity" to an allergen or a substance, as used herein includes "hypersensitive reaction" or "hypersensitivity" to an allergen or a substance.

The term "allergen," as used herein includes any substance that triggers a hypersensitive response.

As will be understood by one of ordinary skill in the art, each embodiment disclosed herein can comprise, consist essentially of, or consist of, its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients or components and to those that do not materially affect the embodiment.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventor intends for the disclosed subject matter to be practiced otherwise than specifically described herein. Accordingly, the disclosed subject matter includes all modifications and equivalents of the subject matter recited in the claims appended hereto as permitted by applicable law. Moreover, any combination of the above-described elements in all possible variations thereof is encompassed by the subject matter unless otherwise indicated herein or otherwise clearly contradicted by context.

The following examples illustrate exemplary methods provided herein. These examples are not intended, nor are they to be construed, as limiting the scope of the disclosure. It will be clear that the methods can be practiced otherwise than as particularly described herein. Numerous modifications and variations are possible in view of the teachings herein and, therefore, are within the scope of the disclosure.

EXAMPLES

Example 1: Auricular Allergy Treatment (AAT), Also Known as Soliman's Auricular Allergy Treatment (SAAT)

The patient's energetic response was evaluated using one the following two parameters, changes in the VAS (Vascular Autonomic Signal) and changes in the bio-energetic field (BEF). The auricular field's resting position was identified using the three phase filter. The allergen in question was then applied on the arm which energetically will add the information of the allergen to the body. The auricular field is re-identified following the application of the allergen.

Changes in the VAS can also help identify the position of the auricular BEF. The three phase filter, also known as the three color filter, can help with the identification of the position where the VAS changes which is the boundary of the auricular energetic field.

A change in the pulse (a positive VAS) was detected which suggested that the patient was allergic or sensitive to the substance being evaluated. For confirmation, an allergy filter was placed on the honeycomb attached to the neck area (parasympathetic) which will energetically remove the information of the allergen from the body. If the auricular field returned to the base line, then the substance being tested was causing an allergic reaction in the patient.

An expanded auricular bio-energetic field was detected which suggested that the patient was allergic or sensitive to the substance being evaluated. The liver's projection area on the ear was then scanned by the white arm of the black and white hammer (the silver arm of the silver and gold hammer) both transversely and vertically in an effort to locate the point of maximum energy emission (positive VAS was detected when the tip of the hammer is directly over the point related to the allergen being evaluated). The tip of the hammer gradually zoomed in on the point of maximum energy emission.

Once the point with maximum energy output was detected, an electrical pointer was applied to confirm that the point was electrically active. A slight indentation with made to mark the point. Alternatively, an acupuncture needle could be inserted in that particular area for marking the point.

Immediately, a 0.3-mm Seirin Spinex temporary needle was inserted at the site. If the temporary needle was inserted at the correct point the bio-energetic field should retract back to the level existing prior to the application of the allergen. If re-evaluation continued to show distress (expanded auricular bio-energetic field), the process was repeated to seek the correct point related to the allergen being evaluated.

Example 2: An Alternative Method of SAAT

While the allergen was in place, the livers projection site was scanned with a point finder to identify the electrically active point related to the allergen. Setting the point finder at a low sensitivity avoids identifying unrelated points. If no points were identified, the point finder's sensitivity was raised slightly and the search is resumed. Once a point was identified, a 0.3-mm Spinex needle was inserted tangentially under the skin to traverse the acknowledged point without impinging on the auricular cartilage. The muscle testing, such as arm strength test or the O-ring test as shown in FIGS. 3A-3C and 4A-4C, was performed while the allergen is still in place. A return of muscle power while still in contact with the allergen confirmed that the auricular point related to the allergen was addressed. Failure to maintain or improve muscle power was indication of needling the wrong point. Once the correct point was identified and needled, a medically adhesive liquid (e.g., Mastisol®) was applied at the site and an adhesive tape is placed to cover the needle.

Example 3: Introduction of the Needle in SAAT

In both of the above methods, the Spinex needle was inserted tangentially under the skin at the identified point in a way that conforms to the regional anatomy of the ear. The body of the Spinex needle traversed the marked point. The needle was removed after three weeks as clinical trials showed that a three week period was an optimal period for clearing the allergic reactions. Patients were instructed to avoid consuming or being exposed to the allergen for the three week period if possible. In cases of food allergy, small doses of the allergen were then tried to see if any reactions still exist. The last step was avoided in cases of anaphylaxis but a conventional allergy test could be done to determine if the patient is no longer allergic to that substance.

In either of the methods, patients were instructed to watch for symptoms and signs of impending infection. Spinex needle would be removed immediately upon experiencing any of the following: unprovoked pain, local heat, swelling, discoloration, itching, and persistent discomfort at the site of insertion.

The immediate removal of the needles would be sufficient to abort the infection process, and substantially reduce the risk of infection.

Both techniques accomplished the desired results for allergy treatment and elimination. Each technique was designed to conform to the expertise and the extent of training of different acupuncturists.

Example 4: Anaphylactic Reaction to Walnut

A nine year old child suffered anaphylactic to walnut while eating at a restaurant. He was attended to by paramedics and taken to a hospital. Later, the child received Soliman's Auricular Allergy Treatment, as described in Example 1, for walnut allergy. The needle was retained in his ear for three weeks. The boy was scheduled to come to the office for removal of the needle after the three week treatment. En route to the office, the child with his mother stopped at his grandfather's place and started eating bread. The mother noticed that the bread was crunchy and discovered that the bread had walnuts. The mother rushed the child to a nearby Emergency Room anticipating another anaphylactic shock. On arriving at the Emergency Room parking lot, the child was sitting in the car calmly with no signs of allergic reaction. The mother declined to go to the Emergency Room and brought the child to the office for needle removal. The child experienced no allergic reaction.

Example 5: SAAT of Patient with Hashimoto Disease

A young female was diagnosed with Hashimoto's disease (an autoimmune disorder of the thyroid gland). The auricular bio-energetic fields was initially identified. A homeopathic preparation of the thyroid gland was placed on the patient's arm. Changes in the VAS and expansion of the auricular bio-energetic field were observed. Examination of the liver's projection site on the auricular acupuncture microsystem suggests possible allergy as an underlying factor for the development of the disease. While the individual was holding the homeopathic preparation of the thyroid gland, the active point was identified and needled with a Spinex intradermal needle. The needle was kept in place for three weeks. Subsequently, evaluation of the patient by her family physician and the blood test indicated that the thyroid gland was functioning at a normal level.

Example 6: SAAT of Patient with Gluten Allergy

A six-year-old boy with known allergy to gluten was brought in for treatment. In the past, the child develops stomach pain and itching of the skin following the ingestion any food item containing "gluten". Skin test in the past identified allergy to gluten. A homeopathic preparation of gluten was placed on the child's arm. The Soliman's allergy zone was scanned for electrically active point or points. One point within the zone was identified to be electrically active. This point was needled with a Spinex intradermal needle. The needle was left in place for three weeks after which the needle was removed. The mother was instructed to reintroduce food containing gluten in small amounts and increasing the amount if there is no sign of an allergic reaction. Subsequent to SAAT, the child was able to tolerate food containing gluten, and skin testing for gluten did not yield any reactions.

Example 7: SAAT of Patient with Allergy to Shrimp

A 25 years old woman was treated for her allergy to shrimp. As soon as the patient eats shrimp, she feels marked tingling around the lips and mouth and experiences the sensation of tightness in her throat. The auricular bio-energetic fields was initially identified. A homeopathic preparation of shrimp was then placed on the patient's hand. The auricular bio-energetic field was rechecked and was identified several inches further away than the baseline identified initially. This was indicative of energetic stress resulting from the placement of shrimp on the individual's hands. The AZ was then scanned for electrical activity. One point within the zone was identified as being electrically active. A temporary acupuncture needle was inserted in that point to determine if it is the correct point that is related to the particular allergy. The auricular bio-energetic field was rechecked and was found to retract to the base line. This was indicative that the point identified related to the allergen. The temporary needle was taken out and replaced by Spinex intradermal needle. The needle was kept in place for three weeks. Following three weeks of treatment, the patient was immediately able to eat shrimp with no reactions appearing.

Example 8: SAAT of Patient with Allergy to Candy Bar

An 18 year old develops a skin rash every time he eats a particular candy bar. Due to the multiple ingredients in the candy bar, the candy bar itself was used to help with treatment of the allergy. Muscle testing was done to appreciate the muscle strength of the patient. The patient then held the candy bar in his hand and muscle testing was repeated. This time considerable muscle weakening was experienced by the patient, which indicated possible allergic reaction. The AZ of the right ear was explored for electrical activity. One particular point was found to be electrically active. A temporary acupuncture needle was inserted in that point to determine if it is the correct point that is related to the particular allergy. Muscle testing was repeated. This time the individual was able to maintain muscle strength despite holding the candy bar. This was indicative that the point identified related to the allergen. The temporary needle was taken out and replaced by Spinex intradermal needle. The needle was kept in place for three weeks. Following the three weeks of treatment, patient was able to eat the candy bar with no allergic reactions.

The methods described herein can be practiced by individuals licensed in acupuncture. This will include licensed acupuncturist and physicians who have received the required acupuncture training. Methods described herein will enable these practitioners to achieve better results for their patients, at lower cost.

The SAAT treatments described are characterized as follows:

A new horizon to the treatment of a very stubborn medical problem that is hardly addressed adequately.

For acupuncture approaches to allergy, these techniques add a new approach to effectively treat and eliminates allergic reactions compared to the current known techniques that are partially effective, not permanent, or flatly unsuccessful.

Permanent relief from allergens.

Safe technique devoid from side effects

Lack of serious complications

Simple technique.

Short period of treatment

Inexpensive

Economical as it will save millions of dollars in health care cost.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. A method of treating allergies, the method comprising, exposing a subject in need of treatment to a suspected allergen,
identifying an allergy zone (AZ) of an acupuncture microsystem of the subject in response to the allergen,
identifying a projection site of liver in the AZ, and
treating the projection site of the liver in the AZ.

2. The method of claim 1, wherein the method further comprises identifying one or more active points in the projection site of the liver and treating the one or more active points.

3. The method of claim 1, wherein treating comprises stimulating the AZ or the one or more active points using a needle, using electrical stimulation, using small pellets, or using small seeds.

4. The method of claim 3, wherein the needle is left in the one or more active points for at least one week.

5. The method of claim 3, wherein the needle is left in the one or more active points for three weeks.

6. The method of claim 1, wherein the acupuncture microsystem comprises ear, hand, face, scalp, foot, tongue, or eye.

7. The method of claim 6, wherein the acupuncture microsystem comprises the ear.

8. The method of claim 1, wherein the suspected allergen is the actual suspected allergen or a homeopathic preparation of the suspected allergen.

9. The method of claim 1, wherein the suspected allergen is from an animal product, a plant, a food, an insect sting, a drug, or a fungal spore.

10. The method of claim 1, wherein the method further comprises evaluating a subject's sensitivity to the suspected allergen prior to step (i).

11. The method of claim 10, wherein evaluating the subject's sensitivity to the suspected allergen comprises muscle testing or observing changes in vascular autonomic signal (VAS) or bio-energetic field (BEF).

12. The method of claim 1, wherein the method further comprises evaluating a subject's sensitivity to the suspected allergen after step (iii).

13. The method of claim 12, wherein evaluating the subject's sensitivity to the suspected allergen comprises muscle testing or observing changes in vascular autonomic signal (VAS) or bio-energetic field (BEF).

14. The method of claim 1, wherein the allergen triggers the production of IgE immunoglobulins.

* * * * *